United States Patent [19]

Hagiwara

[11] 4,298,620
[45] Nov. 3, 1981

[54] TEAR GRASS FERMENTATION PRODUCT, AND PROCESS

[75] Inventor: Yoshihide Hagiwara, Takarazuka, Japan

[73] Assignee: Japan Natural Food Co. Ltd., Osaka, Japan

[21] Appl. No.: 109,213

[22] Filed: Jan. 3, 1980

[30] Foreign Application Priority Data

Jan. 8, 1979 [JP] Japan ................................ 54-129

[51] Int. Cl.$^3$ .............................................. A23L 1/28
[52] U.S. Cl. ........................................ 426/44; 426/52; 426/62; 426/64; 426/580; 426/583; 426/587; 426/599; 426/655
[58] Field of Search ................. 426/44, 49, 425, 431, 426/52, 62, 64, 580, 583, 587, 599, 7, 11, 655; 435/139, 253

[56] References Cited

U.S. PATENT DOCUMENTS 4,180,590 12/1979 Kazuo et al. ...................... 426/44

OTHER PUBLICATIONS

Chemical Abstract 87:165990g, Fermentation Products from Yulmu (Coix Lacryma–Jobi), Sow, Tal Yup, 1974.

*Primary Examiner*—Joseph M. Golian
*Assistant Examiner*—Elizabeth A. Hatcher
*Attorney, Agent, or Firm*—Sherman & Shalloway

[57] ABSTRACT

A product of fermentation of the water extract of tear grass with a Lactobacillus strain, and foods and feeds comprising said fermentation product. The fermentation product containing useful ingredients of tear grass can be produced by inoculating a Lactobacillus strain in a culture medium containing the water extract of tear grass, and subjecting it to lactic fermentation.

5 Claims, No Drawings

TEAR GRASS FERMENTATION PRODUCT, AND PROCESS

This invention relates to a fermentation product of Job's tears, generally called tear grass, which has nourishing characteristics and is edible or potable with improved flavor and palatability, and to its production and utilization. The fermentation product, either alone or as a blend with edible or potable materials, animal feeds, etc., are useful as foods or feeds.

Tear grass, or Job's tears, is a plant belonging to Genus Coix, Tribe Maydeae, Subfamily Panicoideae, Family Gramineae, and is typically named *Coix lachrymajobi Linne* var. mayhen Stapf (Gramineae). Many varieties of it exist. In the present application, all of these are generically called "tear grass". Frequently, the seeds of the above plant are specifically called "tear grass", and the use of the seeds of tear grass is preferred in this invention.

The husked seeds of tear grass are called coicis semen.

During World War II when shortage of food was serious, attempts were made to use the husked seeds of tear grass as substitutes for cereals because of their high carbohydrate, protein and fat contents, or as cereal substitutes in the production of bean jams or miso paste. However, it did not actually gain acceptance as cereal substitutes because it was difficult to obtain in large quantities and was expensive, and particularly, it was difficult to husk and grind and moreover had poor flavor and palatability.

The present inventor has made extensive investigations in order to develop a technique of modifying tear grass to make it fit for eating or drinking by utilizing its nourishing values. These investigations have led to the discovery that a lactic fermentation product of tear grass obtained by inoculating a lactobacillus strain in a culture medium containing the active ingredients of tear grass resulting from the extraction of tear grass with water, and fermenting the water extract of tear grass has good taste and nutriment and is fit for eating or drinking with good flavor and palatability.

It is well known that lactic fermentation products of cereals having much carbohydrates, such as rice flour or wheat flour, often give off offensive odors, and it is actually impossible to produce a curd which has a favorably sour taste, a good flavor and good palatability as in coagulated milk products obtained by fermentation of milk with lactobacilli.

Unexpectedly, the present inventor has found that by inoculating a lactobacillus strain in a culture medium containing the active ingredients of tear grass resulting from its extraction with water, and fermenting the water extract of tear grass in the presence of the lactobacillus, there is formed a fermentation product, as a stable curd similar to a coagulated product of milk, which is free from the troubles described above and has good edibility and potability in regard to flavor and palatability.

It has also been found that the water extract of tear grass has an effect of promoting the growth and proliferation of lactobacilli, and by adding it in the production of a fermentation product of milk with lactobacilli, it produces an effect of promoting fermentation, and increases the nutrient value of the resulting coagulated milk product and improves its flavor and palatability.

It has further been found that by extracting tear grass with hot water in the presence of a starch hydrolase, the concentration of the useful ingredients extracted can be increased, and the operation of separating the extract by filtration can be facilitated. In addition, it has been found that the resulting fermentation product in the culture medium containing the water extract of tear grass can be offered as a lactobacillusfermented food having a good taste and much nutriment, either as such or as a mixture with an edible or potable material, and therefore that it is useful in the field of a wide range of foods.

It is an object of this invention therefore to provide a lactic fermented product of tear grass, which has good edibility and potability and a good taste and much nutriment.

Another object of this invention is to provide a process for producing such a product, and the use thereof.

The above and other objects and advantages of this invention will become more apparent from the following description.

The lactic fermented product of tear grass in accordance with this invention can be produced by inoculating a lactobacillus in a culture medium containing the water extract of tear grass, and fermenting the water extract of tear grass in the presence of the lactobacillus.

The starting tear grass is preferably in the form of seeds, husked seeds, coarsely ground products of these, or flours of these. The culture medium used contains the useful ingredients of tear grass obtained by extracting it with water. The amount of the water extract (solid) of tear grass in the culture medium may vary depending upon the solids concentration of the extract, and as required, it can be adjusted to a suitable one (solids content). The water extract may be used as such, or in the properly concentrated state. Or it is also possible to dry it by a suitable drying means such as freeze-drying (lyophilization), spray drying, hot air drying or vacuum drying, preferably a drying means which can avoid excessive heat, and then to prepare a suitable culture medium by using the dried water extract of tear grass.

Usually, it is preferred to use the water extract (solid) of tear grass in a concentration of at least about 10% by weight based on the total solids content of the culture medium. The concentration of the water extract of tear grass is more preferably at least about 15% by weight, especially preferably at least about 20% by weight, on the same basis. The water extract can be used in such a high concentration as more than about 30% by weight, and even more than 35% by weight. In particular, it is preferred to use a culture medium containing at least about 50% by weight of the water extract of tear grass based on the total solids content of the culture medium.

The extracting temperature at which tear grass is extracted with water to obtain useful ingredients may be varied as desired. Preferably, it is at least about 60° C. to the boiling point of the system.

The amount of extracting water and the extracting temperature can be suitably changed depending upon the type, form, size, etc. of the tear grass used. For example, when the tear grass is in the form of husked seeds, for example about 7 to about 15 parts by weight, preferably about 8 to about 12 parts by weight, especially about 10 parts by weight, of water is added to about 1 part by weight of the tear grass, and the mixture is heated at a temperature of about 90° C. for a period of for example about 60 to about 120 minutes, preferably about 80 to about 100 minutes, especially about 90 minutes. Then, if desired, the mixture is lightly boiled for about 2 to 3 minutes, and by using a filter cloth or any other solid-liquid separating means, a water extract having a solids concentration of about 2 to 4% [W (solids)/V (volume of the extract) %] can be obtained.

The yield of the water extract (solids) differs depending upon the type, form, size, etc. of the starting tear grass. Generally, the yield is progressively higher with coarsely ground materials, ground materials and flour than the original whole seeds. On the other hand, the use of a fine powder of the material causes the extract to become paste-like, and thus tends to reduce the efficiency of filtration and separation of the water extract. It has been found, however, that by extracting tear grass with hot water in the presence of a starch hydrolase preparation, it is possible to increase the concentration of the extract, increase the yield of the extract, and also to reduce the viscosity of the extraction system. Thus, the filtration and separating operations can be performed easily.

Examples of the starch hydrolase preparation include alpha-amylase, malt amylase, diastase, takadiastase, and glucoamylase preparations. Together with these enzyme preparations, cellulase preparations such as cellulase and hemicellulase preparations may be used.

The amount of the starch hydrolase preparation differs depending upon the action, properties and potency of the enzyme preparation used and also upon the properties and quality of the starting tear grass. In many cases, amounts of about 0.1% to about 5.0% by weight based on the starting tear grass are sufficient. For example, a powdery enzyme preparation having a potency of 500 units/g may be used in an amount of about 0.2 to about 0.5% by weight. When the extraction is carried out by using these enzyme preparations, it may be carried out at the optimal temperatures for the activity of these enzymes or at temperatures in the vicinity thereof. The extracting temperature may be changed to several values during the extracting operation, and the extracting operation may be carried out at a substantially constant temperature.

The optimal temperature ranges for activity are, for example, about 75° to about 92° C. for alpha-amylase, about 60° to about 92° C. for malt amylase, about 50° to about 92° C. for diastase, about 50° to about 92° C. for takadiastase, about 40° to about 70° C. for glucoamylase, about 30° to about 60° C. for cellulase, and about 30° to about 60° C. for hemicellulase.

There is no particular restriction on the amount of water used in the extraction of useful ingredients of tear grass. In view of the yield of extraction, etc., the preferred amount of the extracting water is about 5 to about 10 parts by weight per part by weight of the starting tear grass.

If desired, the extraction may be carried out under elevated pressures. The extraction can be performed batchwise, continuously, or by other methods. No particular restriction is imposed on the extracting time. It can be varied suitably according to the method of extraction and the extracting conditions, and is, for example, about 0.5 to about 3 hours. It is also possible to carry out the extraction with stirring.

After the extraction, the extract is collected by separating the liquid layer from the solid layer. Any known liquid-solid separating means known in the art can be used. If desired, the solid-liquid separation and filtration can be facilitated by using an organic or inorganic precipitating agent. At this time, filtration aids and precipitating agents, such as diatomaceous earth, clay and polysodium acrylate, can be utilized. The water extract obtained can be used either as such, or after concentration by known concentrating means which cause a minimum of thermal degradation or after dilution with water. Alternatively, it may be dried into a powder by known drying means which do not appreciably cause thermal degradation, and redissolved to a desired concentration.

When the water extract is used as a powder, the powderization can be carried out by concentration at low temperatures and reduced pressure, drying at low temperature and reduced pressure, spray drying at room temperature or an elevated temperature, or lyophilization.

In the process of this invention, a culture medium containing the resulting water extract of tear grass is used. If desired, other additives and/or edible or potable materials may be included in the culture medium. Such other additives and/or edible or potable materials include, for example, materials which facilitate lactic fermentation, materials which impart tastes and flavors, materials which impart moderate viscousness, jelly-making materials, and materials which impart elastic palatability. Specific examples are animal proteins such as animal milks, condensed milk, skim milk and whey; vegetable protein-containing materials such as soybean curds, juices of green leaves of barley, and a dried product thereof; carbohydrates such as starch, lactose or sucrose; nutriment-fortifying agents such as yeast extract, edible plant extracts, malt extract, fruit juices and water extracts of cereal germs; various perfumes and coloring agents; organic acids; and various edible pastes such as gelatin, agar, carrageenan, tamarind seed paste, sodium alginate, carboxymethyl cellulose, and guar gum. In particular, the addition of lactose facilitates lactic fermentation, increases the rate of fermentation, and the amount of an acid formed.

In the process of this invention, a lactobacillus is inoculated in the aforesaid culture medium, and lactic fermentation is carried out. In one embodiment, the culture medium is heat-sterilized in a customary manner, and a starter obtained by cultivating a lactobacillus strain, for example *Lactobacillus bulgaricus*, in a culture medium containing skim milk is inoculated in a culture medium having a solids concentration of about 10 to about 20% by weight in an amount of about 2 to about 10% based on the volume of the culture medium. Lactic fermentation is carried out at a temperature of about 35° to about 45° C., preferably about 38° to about 40° C., to afford a lactic fermentation product of the water extract of tear grass.

The lactic fermentation temperature may be varied depending upon the type of the lactobacillus strain, whether a single or a plurality of lactobacilli are utilized, etc. Generally, temperatures of about 18° C. to about 50° C. are employed. The pH of the culture medium is frequently about 3 to 4 at the end of fermentation. At the start of fermentation, the pH of the culture medium is, for example, about 4 to about 6.

Known lactobacilli can be used in this invention. Examples include *Lactobacillus bulgaris* (IAM 1120, Institute of Applied Microbiology, University of Tokyo, freely available; AHU 1048–1052 Faculty of Agriculture, Hokkaido University, freely available; IFO 3809, Institute for Fermentation, Osaka, freely available; see JFCC Catalog, 1966 Supplement, page 97), *Lactobacillus acidophilus* (IAM 1043; IAM 1084; AHU 1042–1046; IFO 3831; IFO 3953, freely available; see page 97 of the above Catalog), and *Streptococcus thermophilus* (IAM 1047; IAM 1088; AHU 1109-111; AHU 1176-1190; IFO 3535, freely available; see pages 189–190 of the above Catalog). Useful lactic acid bacteria existing in the intestines of man can also be used. These lactic acid bacteria can be utilized either singly or in a combination of two or more.

The fermentation time may be varied suitably depending upon the type and amount inoculated of the lactic acid bacterium, the concentration of the culture medium, the composition and type of the culture medium, the ratio of the water extract of tear grass to other ingredients of the culture medium, etc., and also upon the type of the desired product. For example, the desired fermentation product can be produced in about 10 to 1000 hours.

The acidity of the fermentation product after the fermentation reaches about 0.7 to 3%, and its pH is frequently about 3 to 4. The fermentation product as obtained is edible, for example in the form of a lactic acid drink or coagulated milk product. Or it can be diluted with sweetenings, thickeners, perfumes, etc. prior to drinking. The fermentation product, and its diluted products may also be used in cold confections and other foods.

It is also possible to dry the fermentation product by a known drying means such as drying at room temperature or lyophilizing, and use it either as such or as a fortifier for a wide range of foods.

Thus, according to this invention, there are provided lactic fermentation products of tear grass or the dried products thereof which have superior edibility and potability with good flavor, palatability and taste and high nutriment. These products can be taken either as such or as blends with other edible or potable materials. The lactic fermentation product of tear grass and its dried product obtained by the process of this invention are useful not only as man's foods, but also as animal feeds and feed additives.

Specific examples of the tear grass-fermented goods containing the lactic fermentation product of the water extract of tear grass as an active ingredient include lactic acid drinks, curds, fruit juice-containing lactic acid drinks, carbonated beverages, lactic bacteria powders (to be used as a seed in the production of fermented milk products). Various foods can be prepared by incorporating the tear grass-fermented liquor, and dried product. For example, they are cold confections such as ice cream or sherbet, candies such as caramel, and taffy, soft candies such as jellies, marshmallows, and chewing gums, jams, marmalade, puddings, creams, instant soup, instant skim milk, and seasonings.

The following Examples specifically illustrate the present invention.

EXAMPLE 1

Water (10 liters) was added to 1 kg of husked and ground seeds of tear grass. The mixture was dipped overnight, heated, and boiled for about 60 minutes. The boiled product was filtered to obtain 8.5 liters of a hot water extract of tear grass. The concentration of the extract was 2.4%, and the solids content was 204 g. The extract was concentrated under reduced pressure to about 1/5 of the original amount to obtain 1.8 liters of a concentrate having a concentration of 12%. The concentrate was boiled lightly for about 2 minutes, and then rapidly cooled to 38° to 40° C. The resulting product was used as a culture medium for lactic fermentation.

Separately, 200 ml of a starter obtained by cultivating *Lactobacillus bulgaricus* (IAM 1120 strain) was provided, and added to the aforesaid culture medium. They were well stirred, and then put into an incubator held at 38° to 40° C. The state of fermentation with time was as follows:

| Time (hours) | Acidity | pH | Number of living bacterial cells |
|---|---|---|---|
| 24 | 0.8 | 3.9 | $5.2 \times 10^8$ |
| 48 | 1.1 | 3.8 | $2.6 \times 10^9$ |
| 72 | 1.3 | 3.6 | $2.8 \times 10^9$ |
| 96 | 1.4 | 3.5 | $2.9 \times 10^9$ |
| 120 | 1.6 | 3.5 | $2.8 \times 10^9$ |

Granular sugar (2.7 kg) was added to the fermentation broth obtained at the end of 120 hours, and the mixture was homogenized at 60° C. to obtain a uniform milky syrup. The syrup was heat-sterilized at 80° C. for 40 minutes to obtain a syrup of lactic fermented tear grass.

EXAMPLE 2

1.0 Liter of the concentrate of the hot water extract of tear grass obtained in Example 1 was mixed with 1.0 liter of a separately prepared 12% suspension of skim milk, and the mixture was sterilized at about 90° C. for about 30 minutes. The mixture was cooled to form a culture medium for lactic fermentation. Separately, 200 ml of a starter obtained by cultivating *Lactobacillus bulgaricus* (IAM 1120 strain) was inoculated in the above culture medium. Lactic fermentation was carried out at 38° to 40° C.

The state of fermentation with time was as follows:

| Time (hours) | Acidity | pH | Number of living bacterial cells |
|---|---|---|---|
| 24 | 1.4 | 3.5 | $2.6 \times 10^9$ |
| 48 | 1.8 | 3.5 | $2.8 \times 10^9$ |
| 72 | 2.3 | 3.4 | $2.9 \times 10^9$ |
| 96 | 2.8 | 3.4 | $2.9 \times 10^9$ |

After the lapse of 96 hours, the fermentation broth was treated by a homogenizer to form a homogeneous milky slurry. Granular sugar (3 kg) was further added, and the mixture was emulsified to obtain a homogeneous syrup. The syrup was heat-sterilized at 80° C. for 40 minutes to form a thick lactic-fermented tear grass drink.

EXAMPLE 3

Water (10 liters) was added to husked and ground seeds of tear grass, and the seeds were dipped overnight. Five grams of a starch liquefying enzyme preparation (Kreistase, a product of Daiwa Chemical Co., Ltd.) was added and dispersed fully with stirring. The mixture was gradually heated and maintained at 75° to 80° C. for about 40 minutes. It was further heated, and boiled gently for 2 to 3 minutes. The mixture was filtered to afford 8.5 liters of a filtrate. The concentration of the extract was 3.0%, and the solids content was 300 g.

The extract was concentrated to about ¼ of the original amount to afford 2.1 liters of a concentrate having a concentration of about 13%. It was lightly boiled for about 2 minutes, and then rapidly cooled to 38° to 40° C. The product was used as a culture medium for lactic fermentation.

Then, 200 ml of a separately provided starter obtained by cultivating *Lactobacillus bulgaricus* (IAM 1120 strain) was inoculated in the culture medium. The mixture was well stirred, and then maintained in an incubator at 38° to 40° C.

The state of the fermentation with time was as follows:

| Time (hours) | Acidity | pH | Number of living bacterial cells |
|---|---|---|---|
| 24 | 1.0 | 3.8 | $7.4 \times 10^8$ |
| 48 | 1.2 | 3.7 | $2.8 \times 10^9$ |
| 72 | 1.6 | 3.5 | $2.9 \times 10^9$ |
| 96 | 2.0 | 3.4 | $2.9 \times 10^9$ |

Granular sugar (1.5 kg) and 1.0 kg of powdery bean jam were added to the fermentation broth obtained after the lapse of 96 hours, and they were homogenized by a homogenizer. The resulting syrup was used as a base for lactobacillus drinks containing living lactobacillus cells.

EXAMPLE 4

Water (10 liters) was added to 1 kg of a powder of tear grass (powder of coicis semen), and with stirring, the mixture was heated and maintained at about 90° C. for 30 minutes. The mixture was allowed to cool, and when its temperature reached about 75° C., a dispersion of 5 g of a starch liquefying enzyme preparation (Kreistase, a product of Daiwa Chemical Co., Ltd.) in a small amount of water was added. With stirring, the mixture was heated, and maintained at about 80° C. for about 40 minutes. Then, the mixture was lightly boiled for 2 to 3 minutes. It was filtered to form about 8 liters of a filtrate. The solids concentration was 7.8 W/V%. Water was added to dilute the filtrate to a concentration of about 6%. Then, 630 g of skim milk and 400 g of lactose were added and mixed uniformly. The mixture was sterilized at 60° C. for 30 minutes. It was then rapidly cooled to about 30° C. to prepare a culture medium for lactic fermentation.

About 400 ml of a separately prepared starter obtained by cultivating *Lactobacillus bulgaricus* (IAM 1120 strain) was inoculated in the culture medium, and maintained at 38° to 40° C. The proceedings of fermentation were as follows:

| Time elapsed (hours) | Acidity | pH | Number of living bacterial cells |
|---|---|---|---|
| 24 | 1.2 | 3.9 | $2.5 \times 10^9$ |
| 48 | 1.8 | 3.6 | $2.7 \times 10^9$ |
| 72 | 2.6 | 3.4 | $3.1 \times 10^9$ |

The resulting fermented liquor was a fermented milk product containing living lactobacillus cells and the components of tear grass suitable for health and beauty treatment. It can be directly taken, or used in various processed foods.

EXAMPLE 5

Water (10 liters) was added to 1 kg of a powder of tear grass (coicis semen powder), and with stirring, the mixture was maintained at about 90° C. for 30 minutes. The mixture was allowed to cool, and when the temperature of the mixture became about 75° C., a dispersion of 5 g of a starch liquefying enzyme preparation (Kreistase, a product of Daiwa Chemical Co., Ltd.) in a small amount of water was added. With stirring, the mixture was heated, maintained at about 80° C. for about 40 minutes, and then lightly boiled for 2 to 3 minutes. The mixture was filtered to obtain 8 liters of a filtrate. The concentration of the extract was 8.27 W/V%. Sterilized water was added to the filtrate to dilute it to a concentration of about 5 W/V%. Skim milk (500 g), 500 g of lactose and 500 g of sugar were added to 10 liters of the diluted liquid, and they were mixed at about 60° C. The mixture was mixed with 800 ml of a separately prepared hot 3% agar solution. The mixture was sterilized at 80° C. for 30 minutes. The mixture was rapidly cooled to about 30° C. Then, 600 ml of a starter obtained by cultivating *Lactobacillus bulgaricus* (IAM 1120) was mixed with the mixture with stirring. The resulting mixture was divided into small portions and put into containers. The containers were sealed and maintained at 37° C. In about 20 hours, the acidity of the product in the containers became about 0.8, and lactic fermented curds containing tear grass extracts and having suitable acid taste and hardness were obtained.

EXAMPLE 6

Edibility test:-

The lactic acid fermented product of tear grass obtained in the same way as in Example 1 was spray-dried to form a powder of the fermentation product of tear grass. Sherbet was made in accordance with the following formulation.

| Formulation | Parts by weight |
|---|---|
| Powder of the lactic fermentation product of tear grass | 4 |
| Granular sugar | 21 |
| Distilled monoglyceride | 0.2 |
| Water | 75.8 |
| Stabilizer (Glyloid 2AG; tamarind seed polysaccharide) | 0.4 |

The sherbet mix of the above formulation was prepared, and homogenized by a homogenizer. It was heat-sterilized at 75° C. for 20 minutes, cooled to 5° C., and frozen for 10 hours in a freezer to obtain sherbet having a fine texture and good palatability.

A panel of 30 girls attending high schools (aged 15 to 17) was organized, and caused to taste the sherbet. The results they reported were as follows:

| Rating | Number of panelists |
|---|---|
| Very tasty | 4 |
| Tasty | 22 |
| Not particularly tasty | 4 |
| Poor taste | 0 |
| Very poor taste | 0 |

What we claim is:

1. A fermentation product consisting essentially of the product of fermentation of the water extract of tear grass, or said extract and at least one member selected from the group consisting of animal milks, condensed milk, skim milk, whey, juices of green leaves of barley, a dried product thereof, starch, lactose, sucrose, yeast extract, malt extract, fruit juices and water extracts of cereal germ, with a Lactobacillus strain.

2. The fermentation product of claim 1 wherein the water extract is obtained by extracting tear grass with hot water in the presence of a starch hydrolase preparation.

3. A process for producing a fermentation product containing active ingredients of tear grass, which comprises inoculating a Lactobacillus strain in a culture medium containing the water extract of tear grass, and subjecting it to lactic fermentation for a period of time sufficient to produce the desired product.

4. The process of claim 3 wherein said water extract is obtained by extracting tear grass with hot water in the presence of a starch hydrolase preparation for a period of time sufficient to produce the desired product.

5. The process of claim 3 wherein said lactic fermentation is carried out at a temperature of about 18° C. to about 50° C. while adjusting the pH of the culture medium at the initiation of fermentation to about 4 to about 6.

* * * * *